United States Patent [19]

Kesling

[11] Patent Number: 4,676,747
[45] Date of Patent: Jun. 30, 1987

[54] TORQUING AUXILIARY

[75] Inventor: Christopher K. Kesling, LaPorte, Ind.

[73] Assignee: TP Orthodontics, Inc., Westville, Ind.

[21] Appl. No.: 893,589

[22] Filed: Aug. 6, 1986

[51] Int. Cl.$^4$ .............................................. A61C 7/00
[52] U.S. Cl. ..................................................... 433/18
[58] Field of Search ........................................ 433/18

[56] References Cited

U.S. PATENT DOCUMENTS

| | | |
|---|---|---|
| 3,087,245 | 4/1963 | Asher . |
| 3,164,901 | 1/1965 | Wallshein . |
| 3,235,965 | 2/1966 | Muir . |
| 3,237,305 | 3/1966 | Hegedus . |
| 3,262,207 | 7/1966 | Kesling . |
| 3,600,808 | 8/1971 | Reeve . |
| 3,975,823 | 8/1976 | Sosnay . |
| 4,037,324 | 7/1977 | Andreasen ........................... 433/26 |
| 4,424,088 | 1/1984 | Wool . |

*Primary Examiner*—Robert Peshock
*Attorney, Agent, or Firm*—Lloyd L. Zickert

[57] ABSTRACT

An improved torquing appliance for use with any orthodontic treatment technique to apply either palatal or labial root torquing forces to any one or more teeth. The auxiliary is in the form of an arcuate wire of highly resilient material such that it will not deform when activated and will tend to return to its passive state, and which includes at least a portion that can be easily secured to a bracket against relative rotation therewith.

15 Claims, 18 Drawing Figures

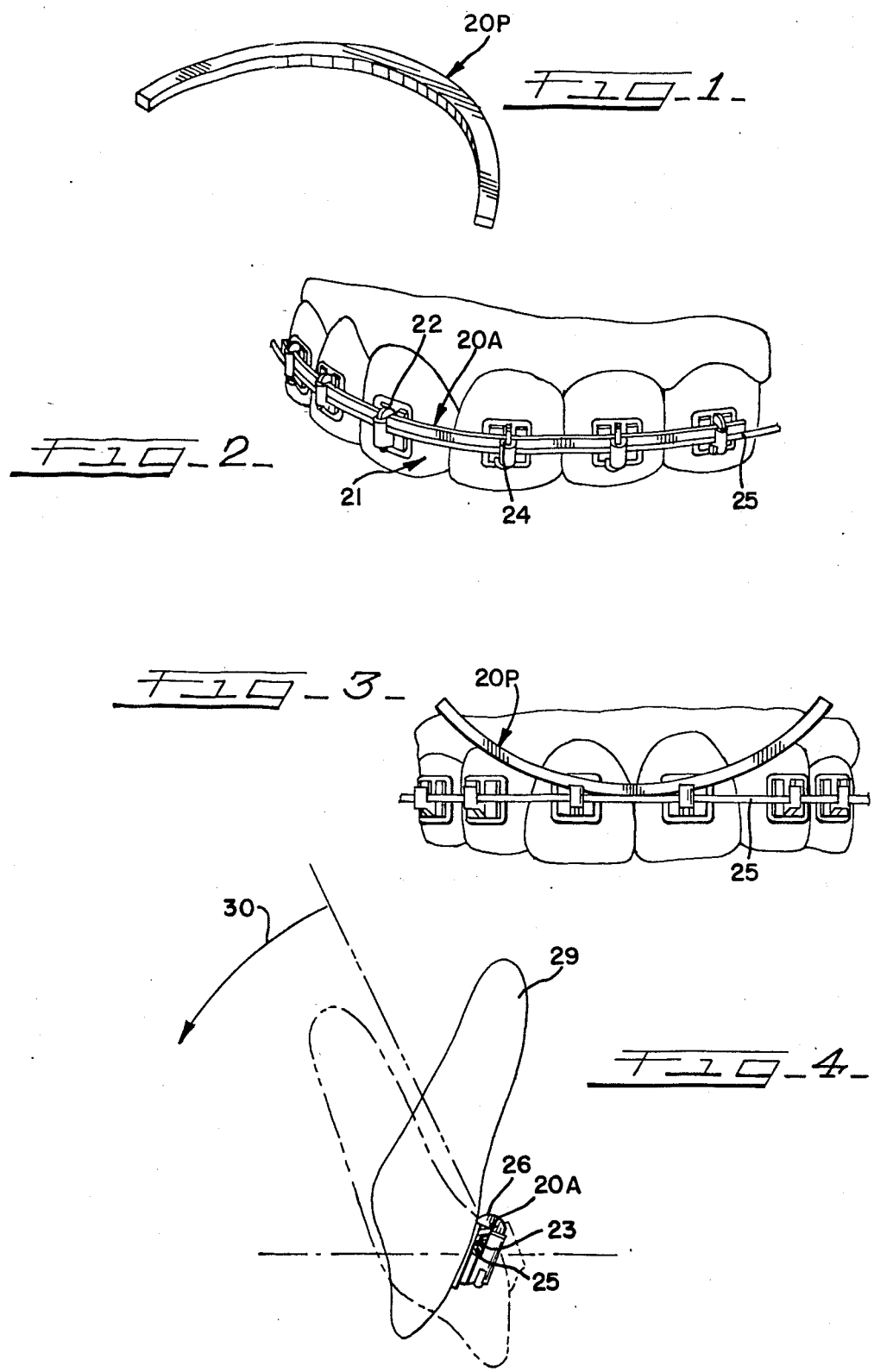

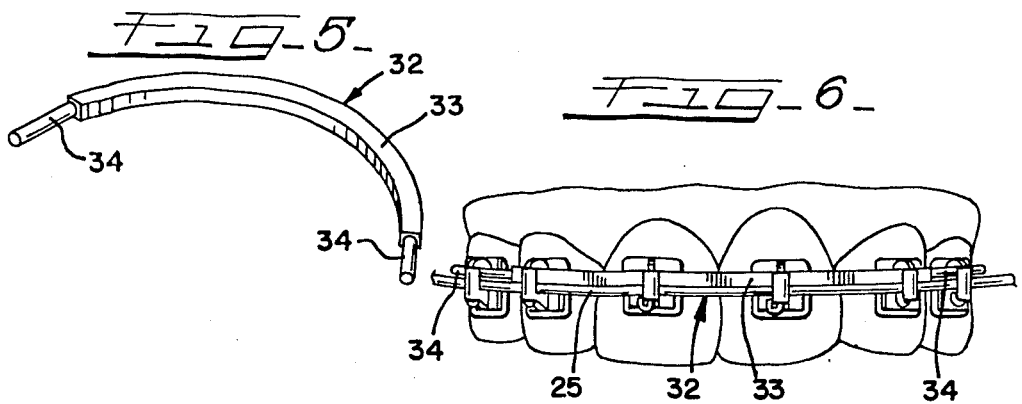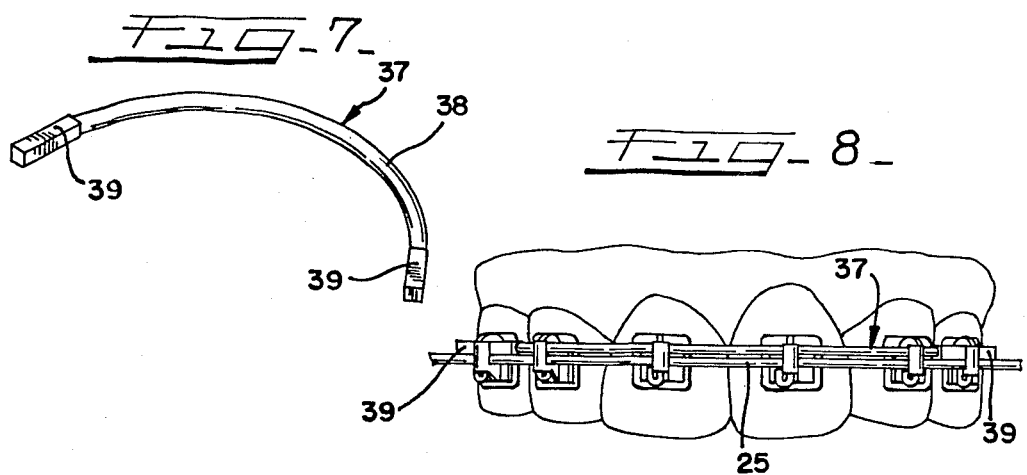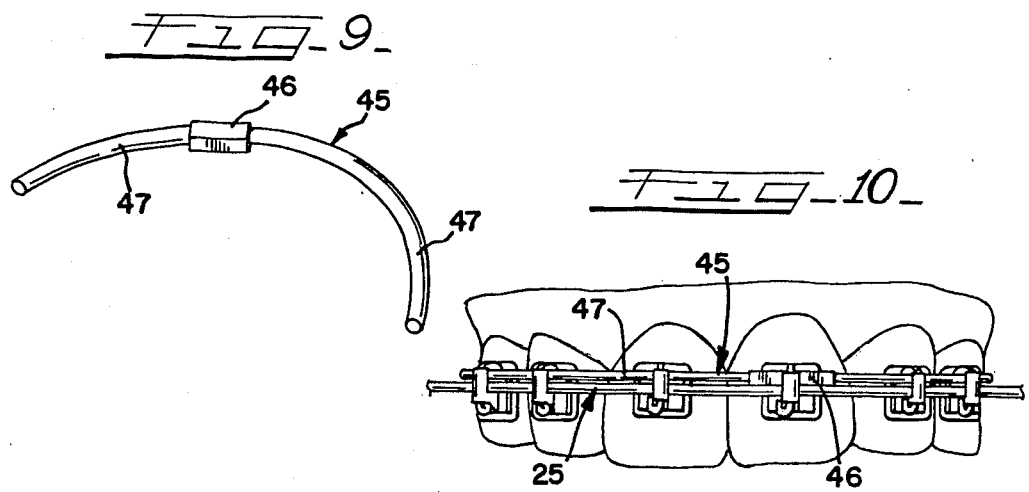

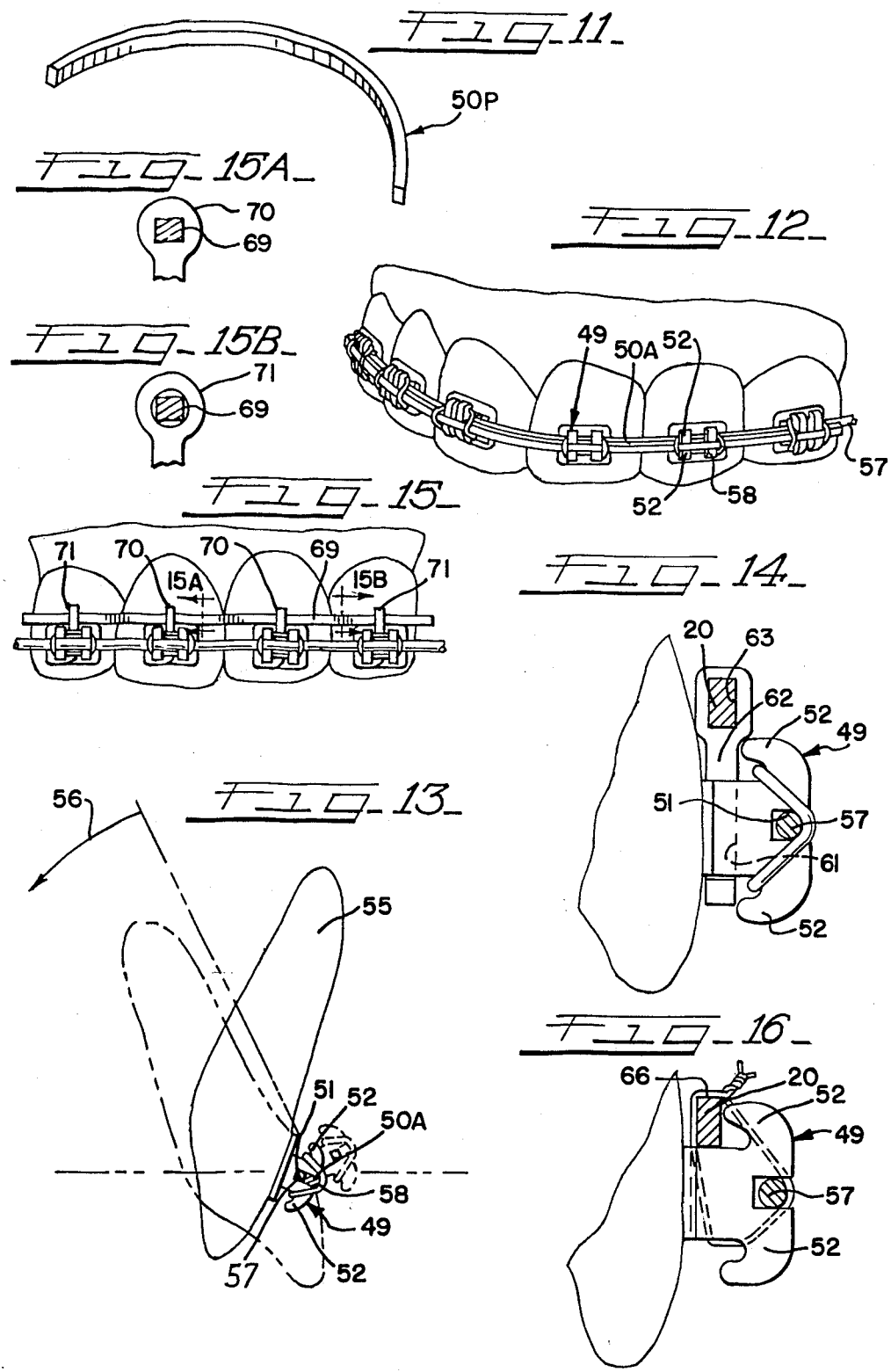

TORQUING AUXILIARY

DESCRIPTION

This invention relates in general to an orthodontic appliance, and more particularly to an improved torquing auxiliary for applying torquing forces to teeth during orthodontic treatment, and still more particularly to an auxiliary made of highly resilient wire that will not deform when activated and which includes at least a portion that is rectangular in cross section.

BACKGROUND OF THE INVENTION

Heretofore, torquing auxiliaries have been in the form of round in cross section wire that is arcuately configured and provided with loops that align with and bear against selected teeth and/or brackets to apply the torquing forces where the auxiliary is secured to a plurality of brackets. It has also been heretofore known to provide torquing springs that are anchored to rectangular wire and include a loop for engagement with a tooth to apply a torquing force. These torquing auxiliaries have been capable of providing either palatal or labial root torquing forces, but in all cases they have defined food traps which are difficult to clean, thereby adversely affecting the mouth hygiene of a patient. Additionally, they detract from the aesthetics of an orthodontic system. Moreover, they quite often require reactivation or adjustment during the period of their use, and they require special skills for proper handling.

SUMMARY OF THE INVENTION

The present invention obviates the disadvantages heretofore encountered in torquing auxiliaries particularly in that it eliminates the vertical loops of heretofore known auxiliaries and the problems and disadvantages attached to those loops. Torquing force generated by the present invention is applied directly to the brackets. Thus, the present invention enhances the mouth hygiene of a person since it does not provide any food traps and makes it much easier for a patient to keep the teeth clean. Further, the present invention looks much better and enhances the aesthetics of an orthodontic system. The auxiliary of the present invention can be used with any type of orthodontic system and is easily adaptable for use with the Begg light wire technique and the various edgewise techniques. It also facilitates the use of uprighting springs which can more easily slide along the archwires and be more easily placed because of the absence of loops.

The auxiliary of the present invention is made of a wire that will not deform when activated and will always tend to resume its original passive shape. Thus, the wire is preferably made of highly resilient or flexible material such as a nickel titanium alloy, a beta titanium alloy, or any other highly flexible stainless steel alloy. It may be made of plastic with or without a metal core. The wire may be solid, twisted or braided and will have at least a portion that is rectangular in cross section or formed to coact with a bracket to apply a torquing force. The word "rectangular" as used herein is intended to cover wire of both the typical rectangular and square cross sections. While the auxiliary of the present invention is primarily intended for applying torquing forces to the anterior teeth, it could be used to apply a torquing force to posterior teeth. It also could be used to torque only a single tooth or simultaneously a plurality of teeth. It is believed advantageous to apply torquing force to that part of the crown to which the bracket is attached.

The auxiliary of the present inention may be secured directly in an archwire slot of a bracket, or it may be connected to a bracket by means of a link such as a pin, or it may be ligated to a bracket so that the portion intending to apply the torquing force is prevented from rotating relative to the bracket.

It is therefore an object of the present invention to provide an improved torquing auxiliary that is devoid of loops and therefore more aesthetically desirable than an auxiliary having loops, and which makes it easier for a patient to maintain teeth cleanliness.

Another object of the present invention is in the provision of an improved torquing auxiliary for applying torquing forces to any of the teeth which is economical to manufacture, and easy to use and mount in a patient's mouth.

A still further object of the present invention is to provide an improved torquing auxiliary that is devoid of any loops and which can be used to apply a torquing force to one or more teeth directly through the brackets.

A still further object of the present invention is in the provision of an improved torquing auxiliary in the form of an arcuately formed length of wire of a highly resilient nature and which when mounted avoids the necessity for adjustment during its use for applying torquing forces.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is a perspective view of the improved torquing auxiliary of the present invention for use with Begg light wire brackets;

FIG. 2 is a fragmentary view of the upper arch showing the anterior teeth with brackets and the torquing auxiliary of the present invention mounted on the brackets;

FIG. 3 is a fragmentary front elevational view of the upper anterior teeth with brackets mounted thereon and illustrating the manner of initially mounting the torquing auxiliary of the present invention in place on the brackets for applying palatal root torque to the teeth;

FIG. 4 is a side elevational view of a tooth having a bracket mounted thereon and showing the torquing auxiliary mounted in place along with a standard archwire and also illustrating the tooth in phantom and depicting the palatal root torquing movement effected by the auxiliary;

FIG. 5 is a perspective view of a modified torquing auxiliary according to the present invention illustrating the distal ends as having a circular cross section which when anchored in brackets will not apply any torquing force to those brackets;

FIG. 6 is a front elevational view of the anterior teeth with brackets mounted thereon and the torquing auxiliary modification of FIG. 5 mounted in place;

FIG. 7 is a perspective view of a still further modified torquing auxiliary of the present invention where only the distal ends are rectangular in cross section and the portion of the auxiliary between the distal ends being round in cross section so as to not apply any torquing force to the brackets where the round section is attached;

FIG. 8 is a front elevational view like FIG. 7 and illustrating the mounting of the modification of FIG. 7 on brackets and depicting the situation where only torquing forces are to be applied to the canines;

FIG. 9 is a perspective view of a further modified torquing auxiliary of the present invention which is useful for applying a torquing force to only a single tooth when mounted on brackets at the anterior teeth;

FIG. 10 is a view similar to FIGS. 6 and 8 and illustrating the mounting of the embodiment of FIG. 9 which will apply a torquing force only to the upper left central although anchored in the brackets of the other anterior teeth;

FIG. 11 is a perspective view of a torquing auxiliary according to the present invention which is applicable for edgewise systems;

FIG. 12 is a view similar to FIG. 2 and showing the embodiment of FIG. 11 mounted in the bracket archwire slots in activated condition for applying torquing forces to the upper anterior teeth;

FIG. 13 is a side elevational view like FIG. 4 but illustrating the use of the edgewise torquing auxiliary shown in FIG. 12 and palatal root torque movement;

FIG. 14 is a greatly enlarged side elevational view of an upper tooth having an edgewise bracket mounted thereon with a vertical slot and showing the torquing auxiliary connected to the bracket by means of a pin having a rectangular opening for receiving the auxiliary wherein the pin is received in the vertical slot of the bracket and held in place;

FIG. 15 is a front elevational view of the anterior teeth including the centrals and laterals with brackets mounted thereon and showing a modified auxiliary together with the type of pins being used for anchoring the auxiliary to the brackets wherein torquing forces are applied only to the centrals;

FIG. 15A is a detailed sectional view taken generally along line 15A of FIG. 15;

FIG. 15B is a detailed sectional view taken generally along line 15B of FIG. 15; and FIG. 16 is an enlarged side elevational view of an edgewise bracket mounted on a tooth and illustrating the manner in which the torquing auxiliary of the present invention may be ligated in place to the tooth for applying a desired torquing force.

DESCRIPTION OF THE INVENTION

The torquing auxiliary of the present invention is in the form of an arcuate wire of a length for applying a torquing force generally to one or more of the anterior teeth, although it could be used to apply torquing forces to any of the posterior teeth. While illustrated only in connection with applying torquing forces to the upper teeth, it will be appreciated that it is likewise useful for applying such forces to the lower teeth. Further, while illustrated in mounted relation only at the labial of the teeth, it could be used lingually in a lingual system. In all cases the wire is of a material that is highly resilient so that it can be activated without distorting the wire whereby it will tend to return to its normal passive state. It is the tendency to return from the activated to the passive state that causes the torquing forces to be applied to the teeth. Mounting the auxiliary on the teeth automatically activates the auxiliary, and unlike heretofore known auxiliaries of all round wire and having loops that may need adjusting, no adjustments are needed during its use.

While the wire may be made of any suitable highly resilient material having the desired memory characteristics, nickel titanium alloy has been found to be quite satisfactory. The objection of the wire is to apply light torquing forces to effect the suitable torquing of one or more teeth in accordance with a prescribed treatment plan. With respect to the upper teeth, the forces will be either palatal root torquing or labial root torquing. With respect to the lower teeth, the torquing forces for anterior teeth will be either lingual root torquing or labial root torquing.

The torquing auxiliary of the present invention is of such a length that it can be secured to a plurality of brackets. The cross-sectional shape of all or any part or parts of the auxiliary determines where the torquing forces will be applied. The portions of the wire to apply torque are formed to fit in the archwire slots of the brackets to prevent relative rotation between the wire and the brackets, or the portions may be mounted in pins or connecting links against relative rotation and the pins are connected to the brackets. While the wire may be solid, twisted or braided, as above mentioned, it further may have a part or all of it cross-sectionally configured for purposes of coacting with the bracket or a pin connected to the bracket to selectively apply torquing forces to one or more teeth. Usually the auxiliary will be mounted in archwire slots of the brackets, although there will be situations where it is more desirable to leave the main archwire alone in the archwire slot and mount the auxiliary in pins which are suitably interconnected to the brackets. The auxiliary is arcuately formed in its passive state and automatically activated when mounted on the brackets like heretofore known auxiliaries. It can be used most effectively in combination with a round archwire with either the Begg or edgewise technique, or any other suitable technique.

It will be understood herein that a torquing force is one that intends to move a tooth about a mesiodistal axis to position it as a predetermined labiolingual inclination from the vertical. Thus, the long axis of the clinical crown will be disposed at a desirable inclination. As above mentioned, the auxiliary is made from a suitable wire having the ability to flex upon being stressed, without deforming, and return to its passive state. Thus, when mounted in the mouth, it will be activated to apply the desired torquing force. In its free or passive state, as mentioned, it will be arcuate between its ends; while in its activated state, it will also be arcuate but turned from its passive state position about ninety degrees so as to apply a torquing force.

The cross-sectional shape of the wire auxiliary, as above noted, will be such as to be connected to at least one bracket against relative rotation for application of a torquing force thereto. Preferably, this shape will be rectangular or square. The auxiliary may be entirely of a rectangular configuration or have sections that are rectangular and other sections that are round, wherein the rectangular sections would be torquing sections, while the round sections would be non-torquing sections. Thus, the rectangular sections would be connected to a bracket against relative rotation with the bracket so that a torquing force would be imparted from the auxiliary through the bracket and to the tooth, while the round sections would be connected to brackets to assist in stressing and activating the auxiliary, but such that they can rotate relative to the bracket so as not to apply any torquing forces to the tooth or teeth on which such brackets are mounted.

An important feature of the torquing auxiliary of the invention is that it does not include any loops as have been present in heretofore known torquing auxiliaries since it is well known that such loops become food traps that are difficult to clean and therefore adversely affect the mouth hygiene. Additionally, such loops may cause injury to the soft tissues of the mouth. It is also known that more adjustments are needed for using an auxiliary with loops. Thus, the auxiliary of the present invention, being devoid of loops, obviates these problems. Additionally, the present invention enhances the aesthetics of an orthodontic system by eliminating unsightly loops and facilitates the ability for springs to be positioned along an archwire.

Referring now to the drawings, and particularly to the embodiment shown in FIGS. 1 to 4, the auxiliary of the invention, generally designated by the numeral 20P when shown in its passive state and 20A when shown in its activated state, is in the form of a length of arcuately formed wire having a rectangular or square cross section. Further, the auxiliary is illustrated in FIGS. 2 to 4 as being used with a Begg or ribbon arch orthodontic system where the brackets generally designated by the numeral 21 and mounted on the anterior centrals, laterals and cuspids are Begg or ribbon arch brackets having a vertical rectangular in cross section archwire slot. These brackets are suitably secured to a base 22 which in turn would be suitably bonded to the teeth. However, it will be appreciated that the brackets may be attached to tooth bands that are in turn cemented to the teeth in a well known fashion. Further, while the auxiliary illustrated spans the centrals, laterals and cuspids, it may only be of a length to span the centrals and laterals.

The bracket 21 is of the type manufactured by TP Orthodontics, Inc. of Westville, Indiana, and identified as the "256 Bracket", which normally is used with a round-in-cross-section main archwire held in place by suitable lock pins. As already noted, the vertical archwire slot 23 is rectangular. A vertically extending pin opening 24 serves to receive a pin for locking the archwire and/or the torquing auxiliary in the archwire slot and to the bracket. As seen particularly in FIG. 4, a round main archwire 25 is first fitted into the base of the archwire slot 23 after which the torquing auxiliary is fitted into the slot and both of which are usually attached or connected to the bracket by means of a lock pin 26, as seen in FIG. 6. Alternately, the auxiliary may be first fitted in the slot followed by the main archwire.

When attaching the auxiliary to the brackets mounted on the upper teeth to produce palatal root torque movement as illustrated in FIG. 4, the plane of the auxiliary in its passive state is vertically disposed with the arcuate curvature opening upwardly, and in the archwire slots of the brackets on the centrals, as seen in FIG. 3. It will be appreciated that preferably the round main archwire is first placed in the slots as shown. The auxiliary, being held against rotation by the central brackets, is essentially turned about ninety degrees from its passive state and forced into the archwire slots of the brackets on the laterals and cuspids and then suitably secured to the brackets in its activated state such as by pinning. When attached to the brackets as described and the plane being essentially turned about ninety degrees from the passive plane, the auxiliary is stressed and activated. It generates a force that urges it back to the passive form in FIG. 1 that produces palatal root torque. For situations where less torque is desired, the auxiliary can be constructed to be stressed when turned fifteen or more degrees from the passive plane. In such a form the auxiliary is bent at fifteen or forty-five degrees or other increment from the horizontal. Once the auxiliary is pinned in the brackets in its activated state, because of its flexibility and tendency to return to its passive state, it will exert forces on each of the brackets and in turn on the teeth to which the brackets are mounted in a direction to apply palatal root torque to the centrals, laterals and cuspids, such as illustrated in FIG. 4 with respect to the central tooth 29. This force will cause it to move from its position shown in solid lines toward the position shown in broken lines and in the direction indicated by the arrow 30. Looking at the cross section of the auxiliary 20A in FIG. 4, activation of the auxiliary when installed on the brackets as above described tends to cause the cross section of the auxiliary to rotate in a counter-clockwise direction and in the direction that the auxiliary would take if returned to its passive state. Continual torquing forces will be applied by the auxiliary until it once again reaches its passive state. While not shown, another version would only span the centrals and laterals to apply torquing forces to these teeth.

It will be appreciated that it is not necessary to form any loops in the auxiliary to obtain the necessary and desired torquing action, and since the auxiliary is rectangular in cross section throughout its length, it will apply a torquing force to all of the brackets to which it is connected against relative rotational movement. Fitting the rectangular auxiliary in the rectangular archwire slots connects the auxiliary to the brackets against relative rotational movement so that the force of the auxiliary is imparted to the brackets and ultimately to the teeth on which the brackets are mounted, and at the area of bracket attachment.

Should it be desired to apply a labial root torque to the teeth, it would then be necessary to mount the auxiliary on the brackets by first disposing the auxiliary with the open end facing downwardly or the opposite to the position shown in FIG. 3. Thereafter, pinning or otherwise connecting the auxiliary to the brackets of the front teeth would stress the auxiliary to generate a force to urge the roots of the teeth to move toward the labial to produce labial root torque.

The auxiliary may also be used to apply torquing forces on the lower or mandibular teeth, it being appreciated that the auxiliary would be mounted to either apply a lingual root torque movement or a labial crown torque movement depending upon how the auxiliary is mounted on the brackets.

Where it would be desired to use the torquing auxiliary of the present invention without applying torquing forces to selective teeth to which the auxiliary is connected, such can be accomplished by providing a round cross section in the auxiliary in the areas to which it is to attach to the brackets of the teeth not desired to be moved. Illustrations of these proposed structures are shown in FIGS. 6 to 10 for a Begg system.

In the embodiment of FIGS. 5 and 6, the auxiliary 32 is shown in its passive state in FIG. 5, and in its activated state when attached to the brackets in FIG. 6. This version includes a centrally disposed rectangular section 33 and round sections 34 at the distal ends. Thus, the rectangular section 33 may also be defined as the torquing section, while the round sections 34 may be defined as non-torquing sections. The dimensions are such that the length of the rectangular section 33 will align and fit in the archwire slots of the brackets mounted on the centrals and laterals, while the round sections 34 will align with and fit in the archwire slots of the brackets mounted on the cuspids. Accordingly, a torquing force is applied to the centrals and laterals and not to the cuspids. Another similar embodiment that is not shown would be an auxiliary spanning only the centrals and laterals which would have a rectangular section or sections engaging the centrals and round sections engaging the laterals to apply torquing forces only to the centrals.

Another embodiment where it is only desirable to apply a torquing force to the cuspids is shown in FIGS. 7 and 8, where the auxiliary identified at 37 is shown in its passive state in FIG. 7 and in its activated state in FIG. 8 for applying torquing forces just to the cuspids. This embodiment includes a centrally disposed round section or portion 38 and rectangular distal sections or portions 39. When mounted on the brackets of the centrals, laterals and cuspids, as shown in FIG. 8, the rectangular portions 39 align with and are received in the archwire slots of the brackets mounted on the cuspids so as to apply a torquing force, while the round portion 38 would be aligned with and received in the slots of the brackets on the centrals and laterals so that no torquing force would be applied to these teeth.

Where it would only be desired to apply a torquing force to a single tooth, the auxiliary would be round except for a relatively short in length rectangular section. Such an auxiliary is illustrated in its passive state in Fig. 9 and in its activated state in FIG. 10 and identified by the numeral 45. This auxiliary includes a rectangular portion 46 and round portions 47. The rectangular portion 46 is disposed on the wire so that it will mate with a bracket on one of the centrals, while the round portions will mate with brackets on the other central, the laterals and the cuspids, as illustrated in FIG. 10. Accordingly, auxiliary 45 will only apply a torquing force to the one central having connected thereto the rectangular portion 46.

It will now be appreciated that the auxiliary may be designed with rectangular and round cross sections for applying selective torquing forces to only those teeth needing torquing movement.

The auxiliary of the present invention can likewise be used for the techniques using edgewise brackets, but in such techniques the auxiliary would be formed so that in the passive state the long dimension of the rectangular cross section will be vertically disposed, rather than horizontally disposed as in the previously described embodiments, when mounting the auxiliary in the archwire slots of the brackets, as illustrated in FIGS. 11 to 13. It may be further appreciated that the form of the auxiliary used with the Begg brackets may also be used in the edgewise technique when the auxiliary is mounted externally of the archwire slot, such as illustrated in FIGS. 14 to 16. In either of the instances just described, it will be appreciated that the main archwire is anchored in buccal tubes in the usual manner and extends over the entire arch, and will normally be round in cross section.

Referring now particularly to FIGS. 11, 12 and 13, this embodiment is shown in its passive state and identified as 50P in FIG. 11, and in its activated state and identified as 50A in FIGS. 12 and 13. The edgewise brackets illustrated may be of any suitable type, but for purposes of simplicity are shown to have the usual horizontal rectangular archwire slot 51 centrally disposed between twin tie wings 52. While the brackets illustrated in FIG. 12 are of the double tie wing type, they may be of the single tie wing type if desired. Since the entire length of the auxiliary 50 is rectangular in cross section when mounted on the brackets 49, a torquing force will be applied to each of the teeth having brackets to which the torquing auxiliary is secured against relative rotational movement. Where it is desired to apply a palatal root torque movement such as to move the tooth 55 in FIG. 13 from the solid line illustration to the broken line illustration in the direction of the arrow 56, the auxiliary is first inserted into the archwire slots of the brackets on the centrals so that the open end faces upwardly and then thereafter flexed and inserted in the archwire slots of the other brackets. It would then be activated to produce palatal root torque. The round archwire could be inserted into the slot first followed by the auxiliary as illustrated or, secondly, after first inserting the auxiliary. Round ligatures 58 would then be applied over the archwires and the tie wings to retain the archwires in place in the bracket slots. If it is desired to provide labial root torque, the auxiliary would be inserted with the open end facing downwardly. As in the previous embodiments, the torquing force is generated by stressing the auxiliary from its passive state whereby it then seeks to return to its passive state.

Where only selected teeth are desired to be torqued, the auxiliary may be formed with rectangular and round sections in a manner already described in connection with the previous embodiments structured for the Begg technique. Where adjacent teeth are desired to be torqued, the auxiliary may have a continuous rectangular section spanning the teeth or individual rectangular sections that would align with the teeth.

The torquing auxiliary of the type formed for the Begg technique can also be used with edgewise brackets. For example, the brackets may be provided with a vertical slot 61 as shown in FIG. 14. A specially designed auxiliary retaining pin 62 having a head with a rectangular opening 63 is mounted in the slot in the usual manner to connect the auxiliary 20 to the edgewise bracket 49. Each of the brackets would include openings or slots for the pins 62 so that the auxiliary 20 can be connected to each bracket. In this arrangement, only the round main archwire 57 would be received in the archwire slot 51 and ligated in place. The pins would be inserted in the pin openings and the tails of the pins bent over the bracket to hold them in place in the same manner that a lock pin is secured to a Begg bracket. Pins of this type could also be used in the Begg system, wherein the pins would lock the main archwire in the archwire slots and have a head of the same type as pin 62 for receiving the auxiliary.

A further system for utilizing the auxiliary of the invention with an edgewise system where edgewise brackets would be employed and pins would be used for connecting the auxiliary to the brackets is illustrated in FIGS. 15, 15A and 15B where the auxiliary is square in cross section throughout its length and generally designated by the numeral 69 and connected to the brackets of the centrals by use of pins 70 having square holes and connected to the laterals by pins 71 having round holes. Here, the torquing force would be applied to the centrals having the square holed pins but not to the laterals which would have the round hole pins as the wire could freely rotate in the round holes. Utilizing the pins 70 and 71 selectively, it will be appreciated that torquing force may be selectively applied to one or more teeth as desired when connecting the auxiliary to the edgewise brackets with such pins. These pins could also be adapted for the Begg system.

Another method of using the auxiliary 20 with the edgewise brackets is illustrated in FIG. 16 wherein the auxiliary is disposed at the upper side of the bracket between the upper tie wing 52 and the tooth and ligated in place by a wire ligature 66 that also ligates the round main archwire 57 in the archwire slot. The auxiliary 20 would fit between the tie wing and the tooth such that it would not rotate and would therefore apply a torquing force. The auxiliary of the invention may be connected in any desired way as to prevent relative rotation between it and a bracket in order to provide a desired torquing force.

While not shown, the auxiliary may be used in other ways with an edgewise system. With respect to the teeth desired to be torqued, the auxiliary may be mounted in the horizontal archwire slot, while the main round archwire could be offset to be either ligated back of the upper wings or mounted in pins received in the vertical slots.

It will be understood that modifications and variations may be effected without departing from the scope of the novel concepts of the present invention, but it is understood that this application is to be limited only by the scope of the appended claims.

I claim:

1. In combination with an orthodontic system for an arch of a person including a plurality of brackets mounted on the teeth of the arch, a main archwire attached to all of said brackets, a torquing auxiliary attached to a plurality of said brackets on a curved segment of the arch for applying a torquing force to a tooth, said auxiliary comprising a wire of highly resilient material such that it will not deform when stressed from its passive or unstressed state and will tend to return to its passive state, said wire being arcuate along its length in its passive or unstressed state and devoid of any loops and having a rectangular cross section therealong where it is attached to at least one bracket against relative rotation therewith and stressed when pulled to the level of the arch and attached to the adjacent brackets to apply torque to the tooth on which the bracket is mounted against rotation, whereby the auxiliary is passive in one position prior to mounting on the brackets and then turned about fifteen to ninety degrees from the passive state and stressed and arcuately formed on the curved segment of the arch in a different dimension than when in its passive state to then be attached to the brackets in the stressed state thereby activating the auxiliary to apply torque to the bracket or brackets to which it is mounted against relative rotation.

2. The auxiliary of claim 1, wherein the wire is of a nickel titanium alloy or material of similar properties.

3. The auxiliary of claim 1, wherein the area of the wire not preventing relative rotation with the bracket or brackets to which it is attached is round in cross section.

4. The auxiliary of claim 1, wherein the area of the wire preventing relative rotation engages a single bracket to apply a torquing force to a single tooth.

5. The auxiliary of claim 1, wherein the area of the wire preventing relative rotation extends to more than one bracket to apply a torquing force to more than one tooth.

6. The auxiliary of claim 1, wherein the area of the wire preventing relative rotation extends to each bracket on which the wire is mounted to apply a torquing force to each tooth to which the brackets are mounted.

7. In combination with an orthodontic system for an arch of a person including a plurality of brackets mounted on the teeth of the arch, a main archwire attached to all of said brackets, a torquing auxiliary attached to a plurality of said brackets on a curved segment of the arch for applying a torquing force to at least one tooth, said auxiliary comprising a wire of highly resilient material such that it will not deform when stressed from its passive or unstressed state and will tend to return to its passive state, said wire being arcuate along its length in its passive or unstressed state and devoid of any loops and having at least one torquing section aligned with a bracket and at least one non-torquing section aligned with a bracket, said torquing section connected to the respective aligned bracket against relative rotation therewith and stressed when pulled to the level of the arch and attached to adjacent brackets to apply torque to the tooth on which the bracket is mounted against rotation, said non-torquing section connected to an aligned bracket for relative rotation therewith, whereby the auxiliary is passive in one position prior to mounting on the brackets and then turned about ninety degrees from the passive state and stressed and arcuately formed on the curved segment of the arch in a different dimension than when in its passive state to then be attached to the brackets in the stressed state thereby activating the auxiliary to apply torque to the bracket or brackets to which it is mounted against relative rotation.

8. The auxiliary of claim 7, wherein said torquing section is rectangular in cross section.

9. The auxiliary of claim 8, wherein said non-torquing section is round in cross section.

10. The combination of claim 9, wherein the brackets include rectangular archwire slots and the auxiliary is mounted and retained in said slots.

11. The combination of claim 9, wherein the brackets include pin openings and the auxiliary is connected to said brackets by pins received in said openings.

12. The combination of claim 9, wherein the auxiliary is ligated to the brackets.

13. The combination of claim 11, wherein the auxiliary is square in cross section and the pins have either square holes for receiving the auxiliary against rotation or round holes for rotation.

14. The combination of claim 13, wherein the brackets are the ribbon arch type.

15. The combination of claim 13, wherein the brackets are the edgewise type.

* * * * *